(12) United States Patent　　　　(10) Patent No.:　US 12,630,888 B2
Zhang et al.　　　　　　　　　　　　(45) Date of Patent:　May 19, 2026

---

(54) SINGLE-NUCLEOTIDE POLYMORPHISM LOCUS SIGNIFICANTLY RELATED TO YARDLONG BEAN ANTHOCYANIN CONTENT, KOMPETITIVE ALLELE-SPECIFIC POLYMERASE CHAIN REACTION MARKERS AND APPLICATION THEREOF

(71) Applicant: Jiangsu Academy of Agricultural Sciences, Nanjing (CN)

(72) Inventors: Hongmei Zhang, Nanjing (CN); Wei Zhang, Nanjing (CN); Shan Meng, Nanjing (CN); Huatao Chen, Nanjing (CN); Xiaoqing Liu, Nanjing (CN); Xin Chen, Nanjing (CN); Xiaoyan Cui, Nanjing (CN); Qiong Wang, Nanjing (CN)

(73) Assignee: Jiangsu Academy of Agricultural Sciences, Nanjing (CN)

( * ) Notice: Subject to any disclaimer, the term of this patent is extended or adjusted under 35 U.S.C. 154(b) by 152 days.

(21) Appl. No.: 18/399,181

(22) Filed: Dec. 28, 2023

(65) Prior Publication Data

US 2024/0229165 A1　　Jul. 11, 2024

Related U.S. Application Data

(63) Continuation of application No. PCT/CN2023/097679, filed on Jun. 1, 2023.

(30) Foreign Application Priority Data

Jun. 7, 2022　(CN) .......................... 202210639446.3

(51) Int. Cl.
C12Q 1/6895　　　(2018.01)

(52) U.S. Cl.
CPC ....... C12Q 1/6895 (2013.01); C12Q 2600/13 (2013.01); C12Q 2600/156 (2013.01)

(58) Field of Classification Search
None
See application file for complete search history.

(56) References Cited

FOREIGN PATENT DOCUMENTS

| | | |
|---|---|---|
| CN | 107475381 A | 12/2017 |
| CN | 108950054 A | 12/2018 |
| CN | 109852723 A | 6/2019 |
| CN | 111910013 A | 11/2020 |

OTHER PUBLICATIONS

Meng et al. Horticulture Research. 11:uhad247, p. 1-10 (Year: 2023).*
GenBank Accession No. CP039354.1 (NCBI Database, National Library of Medicine, National Institutes of Health, available via url: <ncbi.nlm.nih.gov/nuccore/CP039354.1/>, 1 page (Year: 2019).*
Ira A. Herniter et al., "Identification of Candidate Genes Controlling Black Seed Coat and Pod Tip Color in Cowpea (*Vigna unguiculata* [L.] Walp)," G3, Oct. 2018, pp. 3,347-3,355, vol. 8.
Stefano Lonardi et al., "The genome of cowpea (*Vigna unguiculata* [L.] Walp.)," The Plant Journal, Apr. 2019, pp. 767-782, vol. 98.
International Search Report and Written Opinion for PCT/CN2023/097679, mailed Aug. 2, 2023.
Notice of first Office action dated Feb. 24, 2025 in SIPO application No. 202210639446.3.
First search report dated Feb. 18, 2025 in SIPO application No. 202210639446.3.
Notification to Grant Patent Right for Invention dated Mar. 27, 2025 in SIPO application No. 202210639446.3.
Sui Yihu et al., "Dynamic Observation of Some Indexes in Purple Cowpea FZJ-1 During Growth and Development," Journal of Anhui Science and Technology University, Dec. 2018, pp. 12-17, vol. 32, No. 5. doi: 10.19608/j.cnki. 1673-8772.2017.0588 (Translation of abstract included.) Claims involved: 1-10.
Zhang Hongmei et al., "Variation of anthocyanin contents and nutrient component contents in yardlong bean varieties with different pod colors," Journal of Southern Agriculture, Jul. 2017, pp. 1,080-1,085, vol. 48, No. 6. doi: 10.3969/j.issn.2095-1191.2017.06.23 (Translation of abstract included.) Claims involved: 1-10.

* cited by examiner

*Primary Examiner* — Carla J Myers
(74) *Attorney, Agent, or Firm* — Pilloff Passino & Cosenza LLP; Rachel K. Pilloff; Sean A. Passino

(57)　　　　ABSTRACT
An SNP marker significantly related with yardlong bean anthocyanin content is provided in the present disclosure. The SNP marker significantly related with yardlong bean anthocyanin content is located at the position of 2,361,292 bp on chromosome 5 of yardlong bean genome v1.2, with a base A to G substitution, and the nucleotide sequence thereof is shown in SEQ ID NO. 1. KASP marker based on the SNP marker significantly related with the yardlong bean anthocyanin content and application thereof are also provided in the present disclosure. The KASP marker and the SNP marker significantly related with yardlong bean anthocyanin content are applied for molecular marker-assisted selection breeding of yardlong bean anthocyanin traits.

5 Claims, 2 Drawing Sheets

Specification includes a Sequence Listing.

SEQUENCE LISTING

```
Sequence total quantity: 4
SEQ ID NO: 1              moltype = DNA  length = 2248
FEATURE                  Location/Qualifiers
source                   1..2248
                         mol_type = other DNA
                         organism = synthetic construct
SEQUENCE: 1
```

-continued

```
atggatcaaa agcttgtctc aagctggttc catcttcatt cctcagtgcc cttatcctac   60
gtgcaaccac cggaaagcca acctggcatg gtttttcctt ccggcaagaa aatcccggtg  120
gtagatctcg gactgcacga tcgccatgaa atcttgaagc acattttgaa agcctccgag  180
gactatggat ttttccaggt tctttttccc atcaattttc tttccctttg ttgtagttat  240
aatttcacag catatacgcg ctttctgcac tagagataca ataaacaaaa tcaatttcgt  300
cgtaattttt ataagcactg gaatgttatt agtttttgat atcatgaaag tgtcggtgtt  360
taaacttagc tgtttacaat gatttagtt tatgcatgaa aaactgtggt gtaggttatc   420
aaccatggag tatcgaaaga gttaatggat gagacactga atattttcaa ggaatttcat  480
gccatgcctg ctgaagaaaa gataagggaa agttccagag atccaaatgg aggttgcagg  540
ctctacacaa gccgtgagat taacagcaaa gataccgttc agttctggag ggacacatta  600
agacacttgt gtccatcttc tgaagattcc atgcaatttt tgcctcaaaa gcctgcaaaa  660
tatcggtaaa agatcgtctt catttgatgt aattttctg taaataacat tcaatatgag   720
gtatcgtttc ctgtgcaact tatttaaatg agctcacgca acccaattta agtggcttca  780
tcagcgtttt aataaactat aaaccttctt gacaatggta gatatgtact attaatttca  840
gtttgtgtca gatgttttga ctgtggacgt tgatgtgttc tggttgacaa tgatgtctta  900
aaaaatgaca agtcactatc aaaatttttt attccataat tccgtttcat tcttttgaag  960
cataattgac tagtcctatg aatattcttt tagattttct tctaattttt tttaaatgat 1020
tgataatgag attttaacca ttaaacttgg tttaatctga acctttatga gtcatcattg 1080
attgttctga aaggtgagta gacattattc ataccacatg ggcaactaaa ggtgtaatta 1140
actaagacct cttttttctt taccattaag ttttccttca ctgggttgga aaccactacc 1200
actacctaat gttactactt ttgcatctgg tcttaattat cacaaagtca caattaacag 1260
cacacgttta acataagtac cacactgtca tgtcatcatc aatactatag ccgccacttc 1320
acaacgaaca aaaatccagc tcaatacaca ggttagcaca atacaattat taagcataca 1380
cgattgttat taattcatta atttaacaat taaagtttta ttatcttctt cgaaactcat 1440
cttattctga ctaatgaaag attctgttga ctatgatgat tcctctcctt gcagtgaaat 1500
cgttgcaaaa tacacgcaag aaatgagaag aatgggacta aaaatttttgg agctgctatg 1560
tgaaggttta ggacttgacc caaaatactg ttgtggtgga cttagtgaga gtcctttact 1620
gctagctcat cactaccctc catgcccaga accaagttta accttgggag ctcctaagca 1680
cagagatcct aaccttgtta ctattctgct tcaagaaaaa gatataaatg cacttcaagt 1740
cttcaaagat ggagaatgga tagtggttga acctattcct tatgcttttg tggtcaacat 1800
tgggcttatg ttgcaggtaa tatatatatg tttctccata taataataaa ctgtttgata 1860
ttgatatata ttatgtaagt agtatcaatt agcataatat ttgtacactt tttttctgat 1920
acatcaactc attacggaaa acatttggtt cctgattctg ggtcatgatg atatggtttt 1980
gcatgatgaa attctgtgac tgatgaatgt gcaggtgatt agtaatggaa ggttaatcgg 2040
tgctgaacac cgtgtggtga caaattcaga atttgcaagg accacagttg catatttcat 2100
ccgtccaaat agcaaacaga ttatagaacc tgcaaagtgt ttgataagtt ctggtgctca 2160
acctatctac agatccattg catttgaaga gttcttgaaa aatttcatga tcaagggtac 2220
tgatattgaa cgagaattgc tcttgtaa                                     2248

SEQ ID NO: 2              moltype = DNA   length = 44
FEATURE                  Location/Qualifiers
source                   1..44
                         mol_type = other DNA
                         organism = synthetic construct
SEQUENCE: 2
gaaggtgacc aagttcatgc tctgaatatt ttcaaggaat ttca                   44

SEQ ID NO: 3              moltype = DNA   length = 44
FEATURE                  Location/Qualifiers
source                   1..44
                         mol_type = other DNA
                         organism = synthetic construct
SEQUENCE: 3
gaaggtcgga gtcaacggat tctgaatatt ttcaaggaat ttcg                   44

SEQ ID NO: 4              moltype = DNA   length = 20
FEATURE                  Location/Qualifiers
source                   1..20
                         mol_type = other DNA
                         organism = synthetic construct
SEQUENCE: 4
tgggttgcgt gagctcattt                                              20
```

SINGLE-NUCLEOTIDE POLYMORPHISM LOCUS SIGNIFICANTLY RELATED TO YARDLONG BEAN ANTHOCYANIN CONTENT, KOMPETITIVE ALLELE-SPECIFIC POLYMERASE CHAIN REACTION MARKERS AND APPLICATION THEREOF

CROSS-REFERENCE TO RELATED APPLICATIONS

This application is a continuation of PCT/CN2023/097679, filed Jun. 1, 2023 and claims priority of Chinese Patent Application No. 202210639446.3, filed on Jun. 7, 2022, the entire contents of which are incorporated herein by reference.

INCORPORATION BY REFERENCE STATEMENT

This statement, made under Rules 77(b)(5)(ii) and any other applicable rule incorporates into the present specification of an XML file for a "Sequence Listing XML" (see Rule 831(a)), submitted via the USPTO patent electronic filing system or on one or more read-only optical discs (see Rule 1.52(e)(8)), identifying the names of each file, the date of creation of each file, and the size of each file in bytes as follows:

File name: sequence_listing_347135_11562
Creation date: Dec. 23, 2023
Byte size: 6,864

TECHNICAL FIELD

The present disclosure belongs to the field of molecular genetic breeding. Specifically, the present disclosure relates to a single-nucleotide polymorphism locus significantly related to yardlong bean anthocyanin content, kompetitive allele-specific polymerase (KASP™) chain reaction markers and application thereof.

BACKGROUND

As an annual herb with high economic value, yardlong bean is edible in its bean sprouts, seedlings and tender pods, making it one of the important summer leguminous vegetables in China. The yardlong bean is well known for the rich nutrient content and is widely appreciated by consumers, especially the purple-skinned yardlong bean with comparatively high anthocyanin content, which is an excellent health vegetable as well as a source of anthocyanins (Gao Huajic et al., 2010). Anthocyanins possess superb antioxidant capacity, which can help the body to resist certain cancers, cardiovascular diseases, and some diseases related to aging of the organism (Yoshimoto M, et al. 1999; Wang C J, et al. 2000; Kong J M, et al. 2003). The anthocyanin content changes during the development of fruits of plants and varies among different species (Alcalde-Eon C, et al. 2014). During the development of fruits of plants, the content of anthocyanins changes and varies among different species (Alcalde-Eon C, et al. 2014). For people of most countries and regions, vegetables account for a higher proportion of their daily diet than fruits and health products, and therefore it is important to screen and breed some anthocyanin-rich vegetables for the general enjoyment of anthocyanin benefits to human health. Consequently, the study of rapid and effective molecular breeding techniques for anthocyanin traits in yardlong bean is of great importance for molecularly assisted genetic improvement of anthocyanin traits in yardlong bean.

Traditional breeding for high anthocyanin yardlong bean involves single-plant selection based on the anthocyanin content of the breeding progeny, which is time-consuming and labor-intensive as well as susceptible to environmental interference with low accuracy. The development of specific molecular markers for assisted selection utilizing base differences that exist in the target genes is an optimal method to improve the efficiency of selecting yardlong bean with high anthocyanin content. Among them, kompetitive allele-specific polymerase chain reaction (KASP) molecular marker is a new single-nucleotide polymorphism (SNP) typing method based on Amplification Refractory Mutation System (ARMS) and highly sensitive fluorescence detection. The principle is to design two forward primers and one universal reverse primer for the allele SNP site, and each forward primer has specific sequence that binds to different fluorescent markers. The forward primers with sequences that bind to different fluorescent markers and the universal reverse primer PCR amplify the DNA of the samples, and the allelic variants are then reflected by the different fluorescent signals (He C L, et al. 2014). Studies have shown that phycocyanin content is a complex quantitative trait modulated by multiple genes and susceptible to environmental influences (Cavagnaro P F, et al. 2014; Choi Y, et al. 2020). SNP refers to DNA sequence polymorphism caused by variation in a single nucleotide at the genomic level. The SNP significantly related to anthocyanins in yardlong bean can be rapidly and accurately explored by genome-wide association studies (GWAS), which is an effective tool for gene localization.

Accordingly, the development of KASP markers significantly related to yardlong bean anthocyanin content based on identified SNPs closely related to yardlong bean anthocyanins for early (low generation) selection in breeding offers a significant role in reducing the breeding workload and accelerating the breeding progress, as well as an obvious economic benefit. It is particularly important to develop KASP marker for breeding assistance based on the exploration of SNPs significantly related to yardlong bean anthocyanins to realize early molecular-assisted selection of target traits to improve breeding efficiency.

SUMMARY

It is an objective of the present disclosure to identify a single-nucleotide polymorphism (SNP) locus that is significantly related to the anthocyanin content of yardlong bean, and to develop kompetitive allele-specific polymerase chain reaction (KASP) molecular markers and their primer pairs based on the information of the SNP locus, so as to provide technical support for molecular-assisted selection to achieve early identification and screening of this trait.

In order to solve the technical problems, the present disclosure adopts following technical schemes: the present disclosure provides a kompetitive allele specific polymerase chain reaction (KASP) marker based on a SNP marker S05_2361292 significantly related with a yardlong bean anthocyanin content, where a substitution of bases A to G occurs at a position of 2,361,292 bp on a chromosome 5 of a yardlong bean genome v1.2, as shown in SEQ ID NO.1, and a single nucleotide polymorphism mutates from A to G at a 479th position.

The present disclosure also provides a specific primer set for the KASP marker, including a forward primer F1 (SEQ ID NO.2), a forward primer F2 (SEQ ID NO.3) and a reverse primer R (SEQ ID NO.4).

The present disclosure also includes an application of the SNP marker or the KASP marker for the anthocyanin improvement in yardlong bean by marker-assisted selection breeding.

Specifically, in the present disclosure, the KASP marker for SNP marker significantly related with yardlong bean anthocyanin content are applied to an identification or marker-assisted selection, where the method includes determining whether the base at position of 2,361,292 bp on a chromosome 5 of yardlong bean is AA or GG. A yardlong bean with a genotype of GG is selected as a low generation breeding material to provide technical support for molecular marker-assisted breeding of anthocyanin trait of yardlong bean.

In the above method, the specific primer set for KASP marker includes a forward primer F1, a forward primer F2 and a reverse primer R. A PCR amplification is carried out in an ABI7500 real-time fluorescence quantitative PCR instrument. After PCR, the instrument performs genotyping according to a fluorescence signal. After a reaction is completed, the ABI7500 real-time fluorescence quantitative PCR instrument directly read fluorescence data of PCR reaction products, and results of fluorescence scanning are automatically converted into graphics; if the genotyping is not sufficient, the amplification is continued and the genotyping is viewed every 3 cycles until the genotyping is complete.

The present disclosure also includes a use of the SNP marker, the primer set in screening yardlong bean with high anthocyanin content (approximately 100 µg/g).

The present disclosure also includes a method for identification of anthocyanin concentration in yardlong bean, and specifically including following steps:

(1) extracting genome DNA of the yardlong bean to be detected;

(2) using the genome DNA as a template and using the primer set to carry out PCR amplification reaction in a fluorescence quantitative PCR instrument; and (3) performing genotyping according to a fluorescence signal, and determining the yardlong bean to be detected as a yardlong bean with low anthocyanin content (approximately 10 µg/g) when a genotype is AA, and determining the yardlong bean to be detected as a yardlong bean with high anthocyanin content (approximately 100 µg/g) when a genotype is GG.

Among them, a PCR amplification system in step (2) includes: DNA template of a yardlong bean sample, 2×KASP Master mix, KASP Assay Mix, the primer set and water.

Among them, reaction conditions of step (2) include: pre-denaturing at 94 degrees Celsius (° C.) for 15 minutes (min); denaturing at 94° C. for 20 seconds (s), annealing at 61-55° C. for 60 s, reducing a temperature by 0.6° C. per cycle for 10 cycles; denaturing at 94° C. for 20 s, annealing at 55° C. for 60 s, 26 cycles.

The present disclosure also includes a method for screening yardlong beans with different anthocyanin contents, including following steps:

(S1) extracting genome DNA of a yardlong bean plant;

(S2) using the genome DNA as a template, carrying out PCR amplification reaction by using the primer set and detecting whether an SNP genotype is AA or GG; and (S3) selecting yardlong bean plants or strains with different anthocyanin contents in different lineages according to genotypes.

Among them, in step (S1), the genome DNA is extracted by a cetyltrimethyl ammonium bromide method;

among them, in step (S2), the molecular marker primers are first added into the same PCR reaction system, and two blank controls of ultrapure water are set to replace the sample template DNA, and the DNA of yardlong bean recombinant inbred lines (RIL) is amplified by a fluorescence quantitative PCR instrument; the specific amplification system includes: 10 microliters (µL) reaction system, including 2 µL of 25 ng/µL yardlong bean sample DNA template, 5 µL of 2×KASP Master mix; 0.14 µL of KASP Assay Mix including F1:F2:R=2:2:5, 0.14 µL; water 2.9 µL; the reaction conditions include: pre-denaturing at 94° C. for 15 min; denaturing at 94° C. for 20 s, annealing at 61-55° C. for 60 s, reducing a temperature by 0.6° C. per cycle for 10 cycles; denaturing at 94° C. for 20 s, annealing at 55° C. for 60 s, 26 cycles; after the reaction is completed, the fluorescence data of PCR products are directly read by the ABI7500 real-time fluorescence quantitative PCR instrument, and the results of fluorescence scanning are automatically converted into graphics. The molecular marker primers clearly distinguish the two genotypes, where the dot near the Y-axis is the locus carrying the A allele variant with the genotype AA, and the dot near the X-axis is the locus carrying the G allele variant with the genotype GG.

Compared with the prior art, the present disclosure has the following advantages:

in the present disclosure, the SNP marker 05_2361292 significantly related with yardlong bean anthocyanin content is obtained with a 31.66%-38.59% phenotypic variance explained for the first time and is located at the position 2,361,292 bp on the chromosome 5 of the yardlong bean genome v1.2; the GG or AA genotypes are selected from low-generation breeding material to provide technical support for molecular marker-assisted breeding for yardlong bean traits with different anthocyanin contents;

2) the KASP marker developed by the present disclosure distinguish and detect the A or G bases of SNP mutation sites directly and specifically; the KASP marker are of good application for pre-selection and molecular-assisted breeding for anthocyanin content traits in yardlong bean; and 3) the KASP molecular marker primers are used to amplify and genotype 20 yardlong bean lineage materials on a real-time fluorescence quantitative PCR instrument, and the results show that the molecular marker primers can clearly separate the two genotypes, in which the dots close to the Y-axis are the loci carrying the G allelic variant, genotyped as GG, and there are 6 lineages with average anthocyanin contents of 144.13 micrograms per gram fresh weight (µg/g FW) (June 2020) and 126.84 µg/g FW (September 2020); the dot near the X-axis is the locus carrying the A allelic variant, with genotype AA, and there are 14 lineages with average anthocyanin contents of 10.17 µg/g FW (June 2020) and 11.03 µg/g FW (September 2020); and the dot near the origin of the XY-axis is the blank control.

DETAILED DESCRIPTION OF THE EMBODIMENTS

Figure 1:
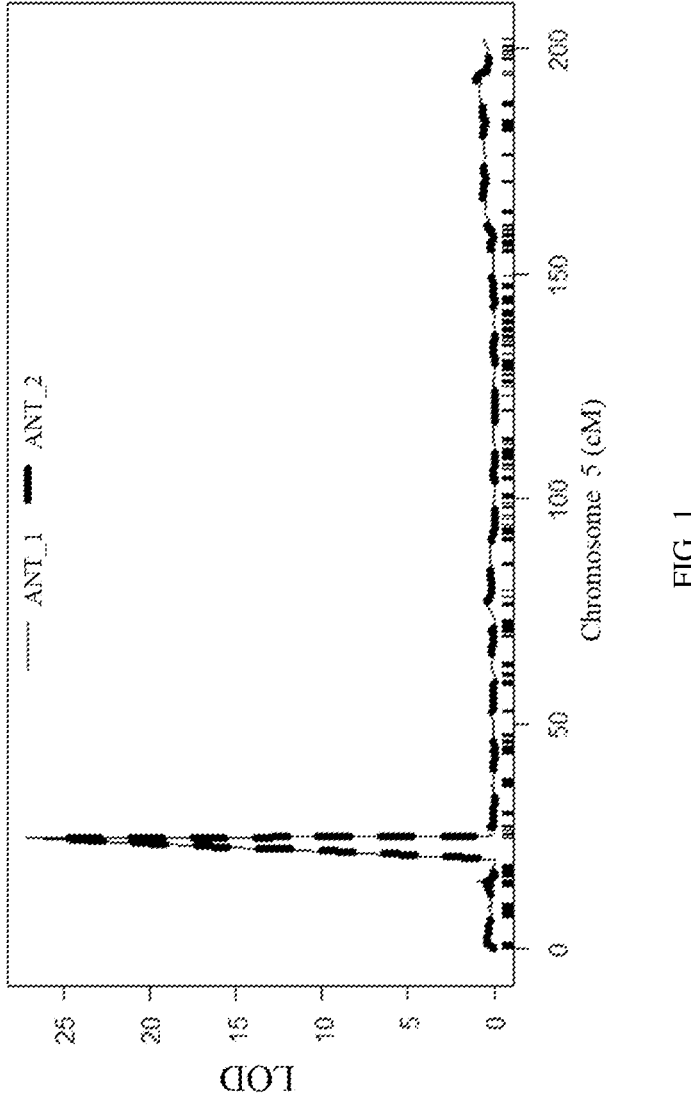
FIG. 1 shows results of quantitative trait locus (QTL) of yardlong bean anthocyanins, including QTL mapping results of anthocyanin content in yardlong bean in June 2020 (Ant 2020-June) and September 2020 (Ant 2020-June).

Embodiment 1 Obtaining SNP locus significantly related to major quantitative trait locus (QTL) of yardlong bean anthocyanin content The SNP marker S05_2361292 significantly related with yardlong bean anthocyanin in the present disclosure is obtained by the following steps:

(1) the "Suzi41" with high anthocyanin content is taken as a female parent (114.99 micrograms per gram fresh weight (µg/g FW)) and the "Sujiang1419" is taken as male parent (10.78 µg/g FW) (Jiangsu Provincial Platform for Conservation and Utilization of Agricultural Germplasm), and the hybrid $F_1$ is obtained, and single plants of $F_1$ generation are self-bred to obtain $F_2$, where a single-grain transmission method is used up to $F_7$ generation to obtain a recombinant self-bred line containing 211 lineages constituting a genetically mapped population; the recombinant inbred population is characterized for anthocyanin phenotypes, and the parental "Suzi41" and "Sujiang1419" are resequenced to a depth of 32.6×, and the recombinant inbred population is sequenced to a depth of 5.44×, and after culling and filtering, an SNP molecular marker map is obtained that covers the whole genome;

DNA extraction and high-throughput sequencing are included: genomic DNA is extracted from young leaves of 2 parents and 211 lineages the yardlong bean population of recombinant inbred lines (RIL) using the CTAB method, and whole genome resequencing is performed.

(2) determination of anthocyanin content of yardlong bean pods in two environments (spring of 2020 and fall of 2020) using UV spectrophotometry:

yardlong bean pods from the parents and lineages of the RIL population are taken and fresh samples of yardlong bean pods from each sample (2 parents and 211 lineages) are thoroughly mixed, crushed and all the seeds are passed through a sieve of 0.25 mm aperture and set aside in sample vials; a sample of 0.5 g of fresh yardlong bean pods is weighed to an accuracy of 0.0001 g and placed in 10 mL of ethanol hydrochloric acid (1:1), followed by anthocyanin determination based on the UV spectrophotometric method; and (3) quantitative trait locus (QTL) localization analysis:

the QTL localization analysis of yardlong bean anthocyanin content data is performed using a mixed linear model (MLM) in the GAPIT algorithm package in R language software, and SNP marker S05_2361292, the major effective QTL locus associated with yardlong bean anthocyanin content, is detected in both environments of June 2020 (sown in April 2020 and pods are collected in June to measure the anthocyanin content in the spring of 2020) and September 2020 (sown in August 2020 and pods are collected in September to measure the anthocyanin content in the fall of 2020), with phenotypic variance explained at a level of 31.66% to 38.59%; located at 2,361,292 bp on chromosome 5 of yardlong bean genome v1.2, three SNP loci significantly related with yardlong bean anthocyanin content are detected, all of which are located on chromosome 5 (see Table 1, FIG. 1).

TABLE 1

QTL localization results for anthocyanin content in yardlong bean RIL population

| Trait | QTL | Chromosome | Marker | Interval (bp) | location (cM) | Confidence interval (cM) | Environment | LOD | Contribution rate (%) | Additive effect |
|---|---|---|---|---|---|---|---|---|---|---|
| Anthocyanin content | qANT5-1 | 5 | bin37 | 2361292-2361292 | 24.6 | 23.1-24.9 | June 2020 | 25.05 | 31.66 | 43.26 |
| | qANT5-1 | 5 | bin37 | 2361292-2361292 | 24.6 | 23.7-24.8 | September 2020 | 26.29 | 35.75 | 46.99 |

Embodiment 2 development of specific primers of KASP markers

Based on the Primer-BLAST function provided by the National Center for Biotechnology Information (NCBI) database of the United States National Library of Medicine, three primers are designed according to the sequence of SEQ ID NO.1, namely, the forward primer F1 (SEQ ID NO.2), the forward primer F2 (SEQ ID NO.3) and the downstream primer R (SEQ ID NO.4), where F1 and F2 respectively include FAM and HEX fluorescent linker sequences (underlined section), and the sequences are as follows:

```
SEQ ID NO. 1:
ATGGATCAAAAGCTTGTCTCAAGCTGGTTCCATCTTCATTCCTCAGTGCCC

TTATCCTACGTGCAACCACCGGAAAGCCAACCTGGCATGGTTTTTCCTTCCGGCAAG

AAAATCCCGGTGGTAGATCTCGGACTGCACGATCGCCATGAAATCTTGAAGCACATT

TTGAAAGCCTCCGAGGACTATGGATTTTTCCAGGTTCTTTTTCCCATCAATTTTCTTT

CCCTTTGTTGTAGTTATAATTTCACAGCATATACGCGCTTTCTGCACTAGAGATACAA
```

-continued

TAAACAAAATCAATTTCGTCGTAATTTTTATAAGCACTGGAATGTTATTAGTTTTTGA

TATCATGAAAGTGTCGGTGTTTAAACTTAGCTGTTTACAATGATTTTAGTTTATGCAT

GAAAAACTGTGGTGTAGGTTATCAACCATGGAGTATCGAAAGAGTTAATGGATGAG

ACACTGAATATTTTCAAGGAATTTCATGCCATGCCTGCTGAAGAAAAGATAAGGGA

AAGTTCCAGAGATCCAAATGGAGGTTGCAGGCTCTACACAAGCCGTGAGATTAACA

GCAAAGATACCGTTCAGTTCTGGAGGGACACATTAAGACACTTGTGTCCATCTTCTG

AAGATTCCATGCAATTTTTGCCTCAAAAGCCTGCAAAATATCGGTAAAAGATCGTCT

TCATTTGATGTAATTTTTCTGTAAATAACATTCAATATGAGGTATCGTTCCTGTGCA

ACTTATTTAAATGAGCTCACGCAACCCAATTTAAGTGGCTTCATCAGCGTTTTAATA

AACTATAAACCTTCTTGACAATGGTAGATATGTACTATTAATTTCAGTTTGTGTCAG

ATGTTTTGACTGTGGACGTTGATGTGTTCTGGTTGACAATGATGTCTTAAAAAATGA

CAAGTCACTATCAAAATTTTTTATTCCATAATTCCGTTTCATTCTTTTGAAGCATAAT

TGACTAGTCCTATGAATATTCTTTTAGATTTTCTTCTAATTTTTTTTAAATGATTGATA

ATGAGATTTTAACCATTAAACTTGGTTTAATCTGAACCTTTATGAGTCATCATTGATT

GTTCTGAAAGGTGAGTAGACATTATTCATACCACATGGGCAACTAAAGGTGTAATTA

ACTAAGACCTCTTTTTTCTTTACCATTAAGTTTTCCTTCACTGGGTTGGAAACCACTA

CCACTACCTAATGTTACTACTTTTGCATCTGGTCTTAATTATCACAAAGTCACAATTA

ACAGCACACGTTTAACATAAGTACCACACTGTCATGTCATCATCAATACTATAGCCG

CCACTTCACAACGAACAAAAATCCAGCTCAATACACAGGTTAGCACAATACAATTA

TTAAGCATACACGATTGTTATTAATTCATTAATTTAACAATTAAAGTTTTATTATCTT

CTTCGAAACTCATCTTATTCTGACTAATGAAAGATTCTGTTGACTATGATGATTCCTC

TCCTTGCAGTGAAATCGTTGCAAAATACACGCAAGAAATGAGAAGAATGGGACTAA

AAATTTTGGAGCTGCTATGTGAAGGTTTAGGACTTGACCCAAAATACTGTTGTGGTG

GACTTAGTGAGAGTCCTTTACTGCTAGCTCATCACTACCCTCCATGCCCAGAACCAA

GTTTAACCTTGGGAGCTCCTAAGCACAGAGATCCTAACCTTGTTACTATTCTGCTTCA

AGAAAAAGATATAAATGCACTTCAAGTCTTCAAAGATGGAGAATGGATAGTGGTTG

AACCTATTCCTTATGCTTTTGTGGTCAACATTGGGCTTATGTTGCAGGTAATATATAT

ATGTTTCTCCATATAATAATAAACTGTTTGATATTGATATATATTATGTAAGTAGTAT

CAATTAGCATAATATTTGTACACTTTTTTTCTGATACATCAACTCATTACGGAAAACA

TTTGGTTCCTGATTCTGGGTCATGATGATATGGTTTTGCATGATGAAATTCTGTGACT

GATGAATGTGCAGGTGATTAGTAATGGAAGGTTAATCGGTGCTGAACACCGTGTGG

TGACAAATTCAGAATTTGCAAGGACCACAGTTGCATATTTCATCCGTCCAAATAGCA

AACAGATTATAGAACCTGCAAAGTGTTTGATAAGTTCTGGTGCTCAACCTATCTACA

GATCCATTGCATTTGAAGAGTTCTTGAAAAATTTCATGATCAAGGGTACTGATATTG

AACGAGAATTGCTCTTGTAA.

Sequence of F1 (SEQ ID NO. 2):
5'-GAAGGTGACCAAGTTCATGCTCTGAATATTTTCAAGGAATTTCA-3';

Sequence of F2 (SEQ ID NO. 3):
                                                          SEQ ID NO. 3
5'-GAAGGTCGGAGTCAACGGATTCTGAATATTTTCAAGGAATTTCG-3';

R sequence (SEQ ID NO. 4):
5'-TGGGTTGCGTGAGCTCATTT-3';

Embodiment 3 Genotype detection of SNP locus in yardlong bean from different lineages and its application The genomic DNA of the 194 lineages of the RIL population is extracted separately, and the PCR amplification products are obtained by using the genomic DNA as a template and the specific primers for the KASP markers of Embodiment 2 in the PCR amplification; PCR amplification is performed in an ABI7500 real-time fluorescence quantitative PCR instrument, which allows genotyping based on the fluorescence signal at the end of PCR; the amplification systems are all 10 μL reaction systems, including: yardlong bean sample DNA template, 25 ng/μL, 2 μL; 2×KASP Master mix 5 μL; KASP Assay Mix (F1:F2:R=2:2:5) 0.14 μL; and 2.9 μL of water. The reaction conditions include: pre-denaturing at 94° C. for 15 min, denaturing at 94° C. for 20 s, annealing at 61-55° C. for 60 s, reducing the temperature by 0.6° C. per cycle for 10 cycles; denaturing at 94° C. for 20 s, annealing at 55° C. for 60 s, 26 cycles.

Figure 2:
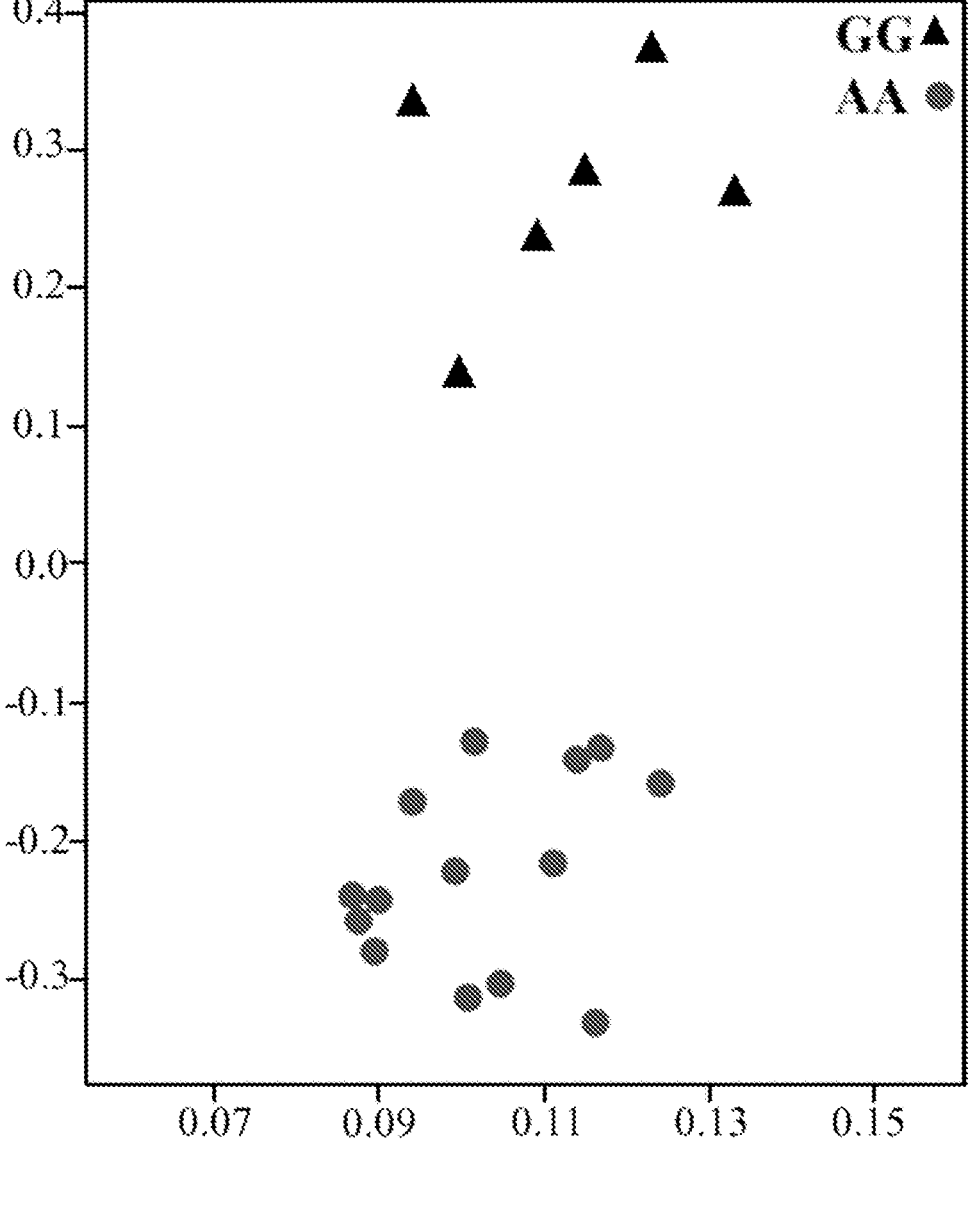
FIG. 2 shows genotyping of different yardlong bean lineages by KASP markers (the black dots near the origin represent the blank control of template-free DNA, the triangle near the Y axis and the black dots near the X axis represent yardlong bean lineages with G allele and yardlong bean lineages with A allele, respectively).

After the reaction is completed, the ABI7500 real-time fluorescence quantitative PCR instrument directly performs fluorescence data reading on the PCR reaction products, and the results are shown in FIG. 2. Twenty lineages of the yardlong bean RIL population are amplified and genotyped using KASP molecular marker primers on a real-time fluorescence quantitative PCR instrument, with results showing that the molecular marker primers are capable of clearly separating the two genotypes, among which the dots near the Y axis are G allele mutation site, and the genotype is GG, with six lineages (lineage numbers SS-11, SS-13, SS-17, SS-22, SS-155, SS-196), and an average anthocyanin content of 144.13 μg/g FW (June 2020) and 126.84 μg/g FW (September 2020); the dots near the X-axis are the locus carrying allele A, and the genotype is AA, with 14 lineages (lineage numbers are SS-44, SS-121, SS-135, SS-138, SS-139, SS-147, SS-148, SS-149, SS-150, SS-151, SS-152, SS-178, SS-198 and SS-201), and an average anthocyanin content of 10.17 μg/g FW (June 2020) and 11.03 μg/g FW (September 2020); and the dots close to the origin of the XY axis are blank controls (Table 2, FIG. 2). It is also found that in the RIL population containing 194 yardlong bean lineages (three lineages at the SNP locus with deletion of the S05_2361292 genotype), the average anthocyanin content of the 94 yardlong bean lineages with the genotype GG is 128.75 μg/g FW (June 2020) and 127.87 μg/g FW (September 2020), respectively; and the average anthocyanin content of the 97 yardlong bean lineages with the genotype of AA is 9.81 μg/g FW (June 2020) and 10.66 μg/g FW (September 2020), respectively (see Table 2); from the above results, it is clear that the yardlong bean with different anthocyanin contents can be screened by determining the genotype AA or GG to determine the level of anthocyanin content of that yardlong bean.

TABLE 2

| | | Anthocyanin content and genotyping table of 194 lineages in yardlong bean RIL population | | |
| --- | --- | --- | --- | --- |
| | Lineage | Anthocyanin content (μg/g FW) | | |
| No. | number | June 2020 | September 2020 | S05_2361292 |
| 1 | SS-4 | 12.52 | 12.55 | A |
| 2 | SS-5 | 7.92 | 8.37 | A |
| 3 | SS-6 | 8.90 | 11.78 | A |
| 4 | SS-7 | 8.49 | 10.93 | A |
| 5 | SS-8 | 5.73 | 7.09 | A |
| 6 | SS-16 | 11.27 | 12.33 | A |
| 7 | SS-19 | 13.22 | 12.75 | A |

TABLE 2-continued

| | | Anthocyanin content and genotyping table of 194 lineages in yardlong bean RIL population | | |
| --- | --- | --- | --- | --- |
| | Lineage | Anthocyanin content (μg/g FW) | | |
| No. | number | June 2020 | September 2020 | S05_2361292 |
| 8 | SS-20 | 8.76 | 9.93 | A |
| 9 | SS-25 | 9.22 | 9.13 | A |
| 10 | SS-26 | 7.99 | 9.05 | A |
| 11 | SS-27 | 7.96 | 8.68 | A |
| 12 | SS-28 | 9.54 | 10.35 | A |
| 13 | SS-29 | 9.54 | 11.30 | A |
| 14 | SS-32 | 9.61 | 10.63 | A |
| 15 | SS-35 | 9.82 | 12.56 | A |
| 16 | SS-40 | 12.53 | 13.36 | A |
| 17 | SS-42 | 12.35 | 13.78 | A |
| 18 | SS-43 | 7.75 | 7.09 | A |
| 19 | SS-44 | 12.28 | 14.49 | A |
| 20 | SS-45 | 12.99 | 17.57 | A |
| 21 | SS-46 | 7.85 | 8.76 | A |
| 22 | SS-47 | 9.37 | 10.05 | A |
| 23 | SS-51 | 12.55 | 14.66 | A |
| 24 | SS-54 | 12.26 | 15.58 | A |
| 25 | SS-57 | 10.04 | 13.12 | A |
| 26 | SS-58 | 13.53 | 14.09 | A |
| 27 | SS-60 | 14.39 | 17.44 | A |
| 28 | SS-61 | 11.78 | 15.23 | A |
| 29 | SS-65 | 11.08 | 11.40 | A |
| 30 | SS-67 | 14.48 | 16.93 | A |
| 31 | SS-75 | 9.82 | 10.05 | A |
| 32 | SS-77 | 9.93 | 11.89 | A |
| 33 | SS-78 | 11.58 | 15.03 | A |
| 34 | SS-81 | 6.73 | 8.11 | A |
| 35 | SS-82 | 7.40 | 9.23 | A |
| 36 | SS-85 | 8.88 | 10.10 | A |
| 37 | SS-89 | 10.26 | 10.65 | A |
| 38 | SS-90 | 9.17 | 11.65 | A |
| 39 | SS-91 | 6.88 | 7.00 | A |
| 40 | SS-92 | 5.51 | 4.44 | A |
| 41 | SS-93 | 8.73 | 8.19 | A |
| 42 | SS-100 | 11.24 | 9.18 | A |
| 43 | SS-101 | 6.55 | 5.75 | A |
| 44 | SS-102 | 8.29 | 9.44 | A |
| 45 | SS-103 | 5.49 | 5.32 | A |
| 46 | SS-104 | 8.29 | 7.02 | A |
| 47 | SS-106 | 7.34 | 6.31 | A |
| 48 | SS-109 | 7.41 | 7.24 | A |
| 49 | SS-110 | 7.58 | 5.77 | A |
| 50 | SS-111 | 7.82 | 8.09 | A |
| 51 | SS-112 | 9.04 | 10.67 | A |
| 52 | SS-114 | 8.60 | 11.62 | A |
| 53 | SS-115 | 9.80 | 11.16 | A |
| 54 | SS-119 | 10.13 | 9.56 | A |
| 55 | SS-120 | 12.37 | 15.81 | A |
| 56 | SS-121 | 11.09 | 10.90 | A |
| 57 | SS-122 | 8.77 | 8.94 | A |
| 58 | SS-125 | 8.25 | 8.74 | A |
| 59 | SS-132 | 8.47 | 8.21 | A |
| 60 | SS-133 | 6.85 | 7.68 | A |
| 61 | SS-135 | 9.68 | 10.09 | A |
| 62 | SS-138 | 10.38 | 10.26 | A |
| 63 | SS-139 | 10.95 | 9.64 | A |
| 64 | SS-143 | 10.00 | 9.72 | A |
| 65 | SS-144 | 8.76 | 9.31 | A |
| 66 | SS-147 | 9.17 | 9.27 | A |
| 67 | SS-148 | 9.31 | 10.69 | A |
| 68 | SS-149 | 9.99 | 10.89 | A |
| 69 | SS-150 | 9.43 | 11.29 | A |
| 70 | SS-151 | 9.26 | 9.51 | A |
| 71 | SS-152 | 8.15 | 9.55 | A |
| 72 | SS-157 | 9.06 | 9.22 | A |
| 73 | SS-158 | 8.56 | 8.81 | A |
| 74 | SS-161 | 9.25 | 9.57 | A |
| 75 | SS-162 | 11.85 | 12.54 | A |
| 76 | SS-164 | 8.65 | 7.73 | A |
| 77 | SS-168 | 10.56 | 8.82 | A |
| 78 | SS-169 | 9.39 | 8.78 | A |
| 79 | SS-171 | 12.40 | 12.02 | A |
| 80 | SS-173 | 11.35 | 11.71 | A |

TABLE 2-continued

Anthocyanin content and genotyping table of 194 lineages in yardlong bean RIL population

| No. | Lineage number | Anthocyanin content (µg/g FW) June 2020 | September 2020 | S05_2361292 |
|---|---|---|---|---|
| 81 | SS-178 | 10.93 | 10.95 | A |
| 82 | SS-179 | 11.81 | 12.44 | A |
| 83 | SS-184 | 10.41 | 10.76 | A |
| 84 | SS-185 | 11.04 | 12.16 | A |
| 85 | SS-188 | 10.67 | 11.80 | A |
| 86 | SS-190 | 13.77 | 15.12 | A |
| 87 | SS-193 | 8.70 | 10.68 | A |
| 88 | SS-194 | 9.75 | 10.69 | A |
| 89 | SS-197 | 15.55 | 11.69 | A |
| 90 | SS-198 | 11.02 | 14.74 | A |
| 91 | SS-199 | 9.07 | 11.74 | A |
| 92 | SS-201 | 10.78 | 12.18 | A |
| 93 | SS-202 | 9.77 | 11.13 | A |
| 94 | SS-203 | 9.90 | 11.52 | A |
| 95 | SS-209 | 11.10 | 13.10 | A |
| 96 | SS-210 | 9.64 | 10.36 | A |
| 97 | SS-211 | 7.91 | 8.56 | A |
| | Average | 9.81 | 10.66 | |
| 98 | SS-1 | 110.94 | 80.66 | G |
| 99 | SS-2 | 221.61 | 223.05 | G |
| 100 | SS-3 | 158.76 | 139.59 | G |
| 101 | SS-9 | 229.93 | 284.62 | G |
| 102 | SS-10 | 70.02 | 70.53 | G |
| 103 | SS-11 | 205.01 | 180.67 | G |
| 104 | SS-12 | 85.42 | 60.95 | G |
| 105 | SS-13 | 111.78 | 89.83 | G |
| 106 | SS-14 | 92.89 | 73.52 | G |
| 107 | SS-15 | 200.62 | 158.35 | G |
| 108 | SS-17 | 128.66 | 119.17 | G |
| 109 | SS-21 | 168.69 | 151.15 | G |
| 110 | SS-22 | 159.54 | 117.40 | G |
| 111 | SS-24 | 86.03 | 73.97 | G |
| 112 | SS-30 | 45.89 | 54.94 | G |
| 113 | SS-31 | 137.21 | 122.16 | G |
| 114 | SS-34 | 10.32 | 12.13 | G |
| 115 | SS-36 | 90.68 | 86.73 | G |
| 116 | SS-37 | 120.10 | 133.85 | G |
| 117 | SS-38 | 118.67 | 126.18 | G |
| 118 | SS-39 | 143.70 | 139.88 | G |
| 119 | SS-41 | 175.89 | 173.46 | G |
| 120 | SS-48 | 155.10 | 174.21 | G |
| 121 | SS-49 | 207.15 | 182.22 | G |
| 122 | SS-50 | 224.73 | 214.89 | G |
| 123 | SS-53 | 120.25 | 137.91 | G |
| 124 | SS-55 | 205.55 | 213.44 | G |
| 125 | SS-56 | 196.10 | 171.64 | G |
| 126 | SS-59 | 180.92 | 111.57 | G |
| 127 | SS-62 | 157.84 | 136.83 | G |
| 128 | SS-66 | 117.60 | 111.92 | G |
| 129 | SS-68 | 154.08 | 107.04 | G |
| 130 | SS-69 | 100.69 | 117.76 | G |
| 131 | SS-71 | 135.33 | 113.25 | G |
| 132 | SS-72 | 193.29 | 208.39 | G |
| 133 | SS-73 | 159.85 | 163.36 | G |
| 134 | SS-74 | 126.35 | 132.78 | G |
| 135 | SS-76 | 14.09 | 17.97 | G |
| 136 | SS-79 | 177.38 | 161.60 | G |
| 137 | SS-84 | 80.76 | 100.09 | G |
| 138 | SS-86 | 184.98 | 218.31 | G |

TABLE 2-continued

Anthocyanin content and genotyping table of 194 lineages in yardlong bean RIL population

| No. | Lineage number | Anthocyanin content (µg/g FW) June 2020 | September 2020 | S05_2361292 |
|---|---|---|---|---|
| 139 | SS-87 | 166.69 | 194.69 | G |
| 140 | SS-88 | 217.82 | 225.73 | G |
| 141 | SS-94 | 70.17 | 51.79 | G |
| 142 | SS-95 | 108.44 | 125.57 | G |
| 143 | SS-96 | 159.00 | 205.90 | G |
| 144 | SS-97 | 185.94 | 168.66 | G |
| 145 | SS-107 | 69.34 | 63.69 | G |
| 146 | SS-108 | 31.63 | 29.63 | G |
| 147 | SS-113 | 31.85 | 24.84 | G |
| 148 | SS-116 | 115.06 | 109.67 | G |
| 149 | SS-117 | 189.74 | 199.45 | G |
| 150 | SS-118 | 52.71 | 49.18 | G |
| 151 | SS-123 | 168.24 | 176.96 | G |
| 152 | SS-124 | 154.54 | 155.93 | G |
| 153 | SS-126 | 115.87 | 129.32 | G |
| 154 | SS-127 | 141.86 | 140.90 | G |
| 155 | SS-128 | 44.14 | 34.74 | G |
| 156 | SS-129 | 47.98 | 50.54 | G |
| 157 | SS-130 | 80.09 | 72.37 | G |
| 158 | SS-134 | 166.21 | 177.67 | G |
| 159 | SS-136 | 45.88 | 48.12 | G |
| 160 | SS-137 | 144.74 | 139.52 | G |
| 161 | SS-140 | 79.66 | 88.60 | G |
| 162 | SS-141 | 85.83 | 99.45 | G |
| 163 | SS-142 | 155.94 | 153.70 | G |
| 164 | SS-145 | 43.50 | 35.35 | G |
| 165 | SS-153 | 151.06 | 133.27 | G |
| 166 | SS-154 | 50.29 | 45.41 | G |
| 167 | SS-155 | 48.80 | 60.44 | G |
| 168 | SS-156 | 40.17 | 43.57 | G |
| 169 | SS-159 | 35.10 | 31.49 | G |
| 170 | SS-160 | 55.52 | 77.31 | G |
| 171 | SS-163 | 151.92 | 165.04 | G |
| 172 | SS-165 | 60.32 | 72.32 | G |
| 173 | SS-166 | 161.17 | 187.82 | G |
| 174 | SS-167 | 111.60 | 107.66 | G |
| 175 | SS-170 | 170.21 | 171.43 | G |
| 176 | SS-172 | 165.73 | 191.53 | G |
| 177 | SS-175 | 278.83 | 375.39 | G |
| 178 | SS-176 | 207.57 | 255.09 | G |
| 179 | SS-177 | 150.63 | 179.18 | G |
| 180 | SS-180 | 40.81 | 64.34 | G |
| 181 | SS-181 | 170.84 | 157.05 | G |
| 182 | SS-186 | 148.57 | 134.37 | G |
| 183 | SS-189 | 191.77 | 150.59 | G |
| 184 | SS-191 | 49.57 | 31.68 | G |
| 185 | SS-195 | 43.22 | 37.39 | G |
| 186 | SS-196 | 211.01 | 193.53 | G |
| 187 | SS-200 | 142.21 | 131.25 | G |
| 188 | SS-205 | 121.56 | 124.70 | G |
| 189 | SS-206 | 206.31 | 199.03 | G |
| 190 | SS-207 | 141.40 | 106.37 | G |
| 191 | SS-208 | 159.27 | 172.57 | G |
| | Average | 128.75 | 127.87 | |
| 192 | SS-18 | 186.01 | 155.39 | — |
| 193 | SS-52 | 75.42 | 14.78 | — |
| 194 | SS-204 | 9.91 | 9.96 | — |

What is claimed is:

1. A set of primers based on a single nucleotide polymorphism (SNP) marker significantly related with a yardlong bean anthocyanin content, the set of primers comprising:

a forward primer F1 consisting of the sequence of 5'-gaaggtgaccaagttcatgctctgaatattttcaaggaatttca-3' (SEQ ID NO: 2);

a forward primer F2 consisting of the sequence of 5'-gaaggtcggagtcaacggattctgaatattttcaaggaatttcg-3' (SEQ ID NO: 3); and a reverse primer R consisting of the sequence of 5'-tgggttgcgtgagctcattt-3' (SEQ ID NO: 4).

2. A method for detecting the level of anthocyanin content in a yardlong bean comprising the following steps:

(a) extracting genomic deoxyribonucleic acid (DNA) of the yardlong bean to be detected;

(b) using the genomic DNA as a template, performing a polymerase chain reaction (PCR) amplification reaction in a fluorescent quantitative PCR instrument with the set of primers according to claim 1 to produce an amplification product; and (c) performing genotyping according to fluorescent signals detected by the fluorescent quantitative PCR instrument in step (b) using the set of primers according to claim 1 to detect the presence of an A or a G at a SNP in the amplification product, wherein the SNP is located at position 479 with respect to SEQ ID NO: 1, and wherein when the genotype is AA, the yardlong bean has low anthocyanin content; and when the genotype is GG, the yardlong bean has high anthocyanin content.

3. The method for detecting the level of anthocyanin content in yardlong bean according to claim 2, wherein a PCR amplification reaction in the step (b) comprises: yardlong bean sample DNA template, the primer set according to claim 1, and water.

4. The method for detecting the level of anthocyanin content in yardlong bean according to claim 2, wherein reaction conditions in the step (b) comprise pre-denaturing at 94 degrees Celsius (° C.) for 15 minutes (min); denaturing at 94° C. for 20 seconds (sec), annealing at 61-55° C. for 60 sec with each cycle decreasing by 0.6° C., for 10 cycles; and denaturation at 94° C. for 20 sec, and annealing at 55° C. for 60 sec, for 26 cycles.

5. A method for screening for yardlong bean with high anthocyanin content, comprising the following steps:

(a) extracting genomic DNA of yardlong bean plants; and (b) using the extracted genomic DNA as a template to perform a PCR amplification reaction with the set of primers according to claim 1 to produce an amplification product and detecting an A or a G at a SNP marker in the amplification product, wherein the SNP marker is located at position 479 with respect to SEQ ID NO: 1;

wherein yardlong bean plants having genotype GG at the SNP marker are selected as plants with high anthocyanin content.

* * * * *